United States Patent [19]

Romer

[11] Patent Number: 4,895,808
[45] Date of Patent: Jan. 23, 1990

[54] METHOD AND APPARATUS FOR ADSORPTION DETECTION

[75] Inventor: Thomas R. Romer, Washington, Mo.

[73] Assignee: Romer Labs, Inc., Washington, Mo.

[21] Appl. No.: 224,159

[22] Filed: Jul. 26, 1988

[51] Int. Cl.$^4$ ............................................. G01N 30/14
[52] U.S. Cl. .................... 436/178; 73/61 R; 73/863.21; 73/863.23; 73/863.86; 210/662; 422/72; 422/73; 422/101; 436/66; 436/67; 436/70; 436/177
[58] Field of Search ...................... 436/66, 67, 70, 177, 436/178; 422/72, 73, 101; 73/61 R, 863.21, 863.23, 863.86; 210/662

[56] References Cited

U.S. PATENT DOCUMENTS

| | | | |
|---|---|---|---|
| 3,512,940 | 5/1970 | Shapiro | 422/101 |
| 3,693,804 | 9/1972 | Grover . | |
| 3,832,141 | 8/1974 | Haldopoulos | 422/101 |
| 3,846,077 | 11/1974 | Ohringer | 422/101 X |
| 3,873,449 | 3/1975 | Connelly et al. | 422/101 X |
| 3,932,277 | 1/1976 | McDermott et al. | 436/177 X |
| 4,022,576 | 5/1977 | Parker | 436/177 |
| 4,189,385 | 2/1980 | Greenspan . | |
| 4,268,270 | 5/1981 | Gabbay et al. | 436/67 |
| 4,679,737 | 7/1987 | Romer | 241/29 |

OTHER PUBLICATIONS

ADAC Official Methods of Analysis (1984)§26.020-26.025 Holiday-Velasco Method, Aflatoxins.
ADAC Official Methods of Analysis (1984)§26.014-26.019 Romer Method Aflatoxins.

Primary Examiner—Barry S. Richman
Assistant Examiner—Jill Johnston
Attorney, Agent, or Firm—Robbins & Robbins

[57] ABSTRACT

A method and apparatus for adsorption and detection of adsorbents or analytes. The method and apparatus can be employed in the field for rapid adsorption of analytes and is particularly useful for detection of mycotoxins. A sample to be analyzed is prepared in solution and placed in a test tube. A tube-like adsorption column having a seal and a valve member is forcefully fed into the test tube to force solutions through the valve member into the column and through a filter and adsorbent to trap interference. The semi-purified solution may then be analyzed for the presence of analytes. The column with the purified solution may be further employed with a second smaller adsorption column similarly equipped with a seal and valve member fitting within the first column. In similar fashion the second column may be forced into the first column to expel the solution therein into the second column and through one or more selective adsorbents for different analytes such as one or more mycotoxins. Detection of the adsorbed analyte may be made by shining a fluorescent or "black" light on the adsorbent which fluoresces to indicate presence of the analyte.

22 Claims, 2 Drawing Sheets

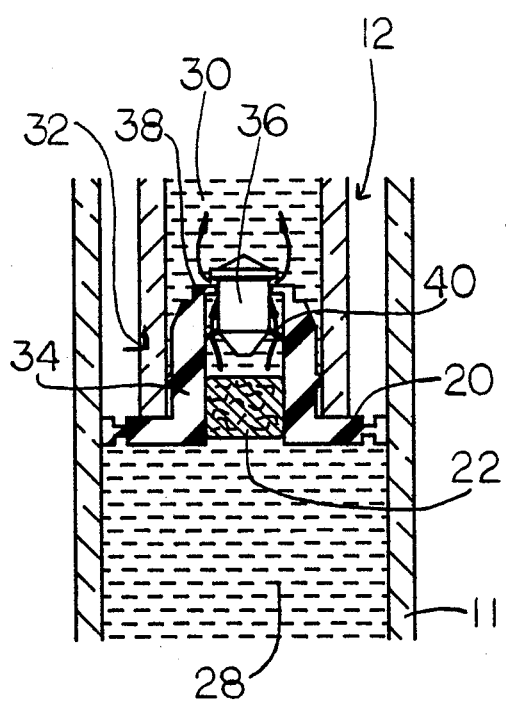
FIG. 5
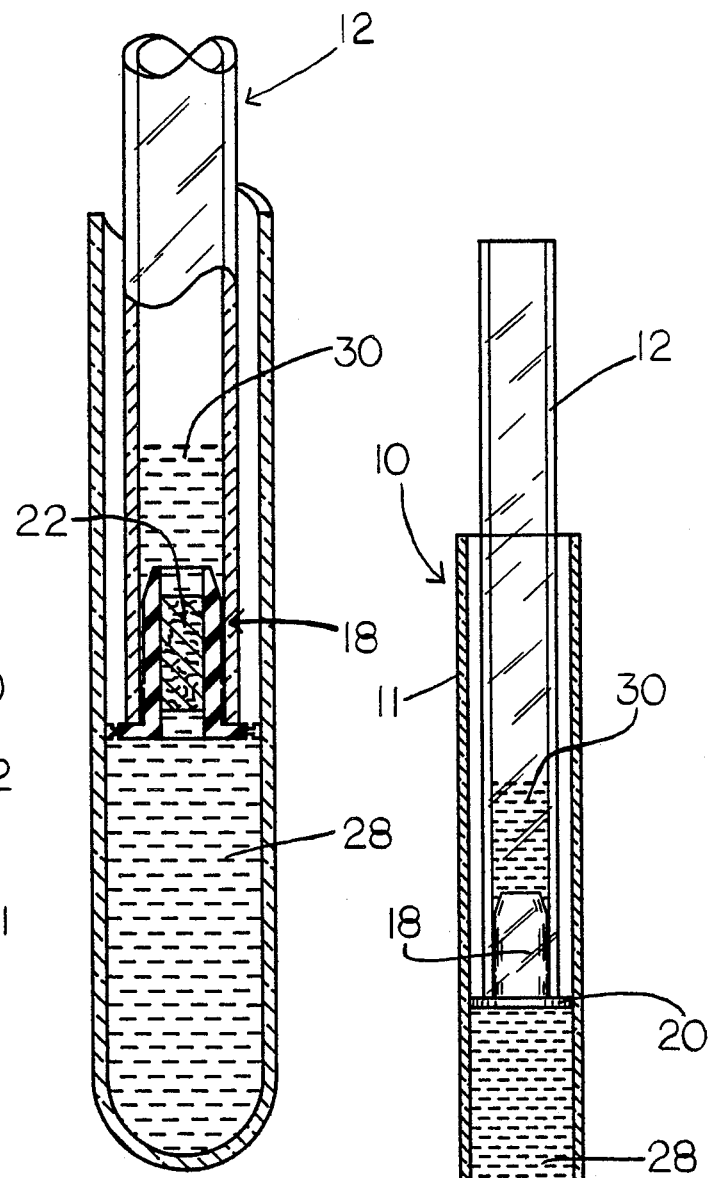
FIG. 4
FIG. 3

METHOD AND APPARATUS FOR ADSORPTION DETECTION

BACKGROUND OF THE INVENTION

In the past, adsorption techniques have been conventionally employed for adsorption of various analytes from solutions by liquid chromatography. This technique consists of two major components, a solvent system and an adsorbent packing material such as an adsorbent of silica gel or aluminum oxide, ion exchange resins or molecular sieves.

Conventionally the solvent system or solution with organic material to be analyzed is passed through the packing material by using some type of differential pressure or force such as by gravity, vacuum pressure, compressed gas, centrifuging or the like. Thus, where time for analysis should be kept short, this necessarily entails costly and space-consuming equipment such as vacuum pumps, valves and gauges, compressed air tanks, centrifuges or the like and a source of energy.

Analysis in the field or away from a laboratory is difficult, time consuming and expensive using known equipment. As an example, analysis of various feed grains and food stuffs for the presence of mycotoxins of one type or another must conventionally be made in the laboratory where sophisticated equipment is readily available. Such mycotoxins are, in minute quantities, potent toxins and carcinogens and require analysis and detection for safeguarding feed grains and the like. There exists a need in the field for a method and apparatus for ready detection of various analytes such as mycotoxins where the detection may be made rapidly and simply and with confidence.

SUMMARY OF THE INVENTION

By means of this invention there has been provided a method and apparatus for rapidly and simply performing adsorption analysis of solutions in the field. Rapid separation of the analytes from interferences in the test solution is effected by a piston-like pressure exerted by the adsorption column employed with a test tube sample of the solution.

The applied pressure forces a test solution containing many organic chemicals through an adsorbent packing material in the adsorption column. The adsorption column operates in the manner of a piston or plunger when inserted and pushed into a test tube filled with the test solution to force the solution through a valve member at the bottom of the column through the packing material. The column has a peripheral rubber flange which acts as a seal to prevent escape of solution or air.

When the desired amount of solution has been forced from the test tube into the adsorption column the semi-purified solution in the column may be analyzed by conventional methods for the presence of the analytes to be detected.

By means of this invention such further analysis may be made in the field without resort to a laboratory. A second smaller adsorption column is employed, similar in construction to the first column described above but having a smaller diameter such that it may be insertable in the first column. This second column may have a similar valve member and flanged seal to operate as a piston or plunger to force the semi-purified solution from the first column into the second column past one or more selective adsorbents therein.

The adsorbent in the second column may be a selective adsorbent which will preferentially adsorb a known analyte to be detected. One or more of such selective adsorbents may be employed in the second column in separate bands for ready detection of the presence of such analytes. Visual observation by change of color of the separate adsorbents may be employed to verify such analyte presence. A fluorescent light, or "black light", using different wave lengths from a light source may also be used for such detection. Comparison against a test standard may also be employed to indicate the detection and allowable level of concentration of the analyte in the test sample. Such detection is extremely helpful in the field where, for example, detection of presence of mycotoxins at a level of 20 parts per billion, i.e., p.p.b., must be routinely made to determine proper and safe levels of concentration.

The test tube and adsorption columns are designed for ready and efficient use in the field by operators such as feedmill operators, farmers and other operators without the requirement of long and arduous laboratory training. The apparatus may be made in kit form and because of the low cost may be disposable which adds to the safety in usage in handling carcinogens and other toxic solutions.

The above features are objects of this invention. Further objects will appear in the detailed description which follows and will be further apparent to those skilled in the art.

For the purpose of illustration of this invention a preferred embodiment thereof is shown in the accompanying drawing. It is to be understood that the drawing is for purpose of description only and that the invention is not limited thereto.

IN THE DRAWING

FIG. 3 is a view partially in longitudinal sections showing the adsorption column in a test tube;

FIG. 4 is an enlarged fragmentary view in section taken similarly to FIG. 3 and showing a two-way valve in the column; and FIG. 5 is an enlarged fragmentary view in longitudinal section showing the adsorption column in a test tube and a one-way valve used in the adsorption column.

DESCRIPTION OF THE INVENTION

In a liquid chromatographic system the separating power is based on the different flow rates that organic molecules will pass through the adsorbent packing material. A solution containing two or more organic materials is forced by pressure of one type or another through the packing material with the amount of force depending upon the particle size of the organic molecules and the desired flow rate. The desired flow rate of the solvent system is determined by the length of time it takes the organic molecules desired to be adsorbed, which are termed analytes, to equilibrate and reach a steady state between the packing material and the solution.

If the flow rate is slow enough the organic analyte will pass through the packing in a band so that at any given time each analyte will cover only a small portion of the packing. As an example, if an orange pigment is being separated from a green pigment by passing a solution of methanol containing these pigments through 40 micron silica gel in a test tube, two narrow bands, one orange and one green, should be seen moving down the packing at different flow rates. As each of these pigments reaches the bottom of the packing, the solution of methanol may be collected in two parts, one containing the green pigment and the other containing the orange pigment. Should the flow rate be too fast, the orange and green bands will broaden and may overlap, thus, preventing complete separation.

A typical flow rate in an adsorption or chromatographic column is about 1 ml per minute. In some cases, various undesired organic compounds termed interferences are left on the column packing while the desired analytes are collected in a semi-purified solution and may be detected and quantitated by a subsequent procedure.

In the instant invention a simple mechanical device in the nature of a plunger or piston is employed to force the test solution from a test tube through the adsorption column which provides for a rapid separation and detection of the analytes from interferences in the solution. This device provides the pressure required to force the solution which may contain various organic chemicals through a packing material which provides for rapid equilibration of interferences in the test solution.

In the instant invention and as an example, an aqueous-organic extract of acetonitrile and water of foods, feeds and ingredients such as corn and soybean meal may be prepared and analyzed. By the use of the plunger type adsorption column and proper packing material a rapid flow rate of about 10 ml per minute can be used which greatly reduces the time required for analysis.

Figure 2:
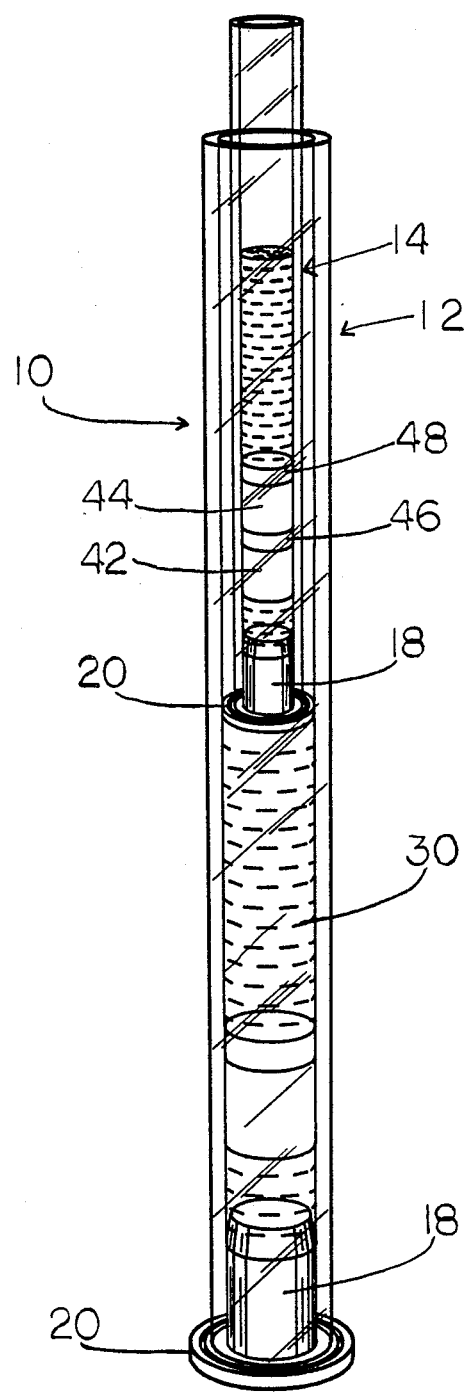
FIG. 2 is a view similar to FIG. 1 but showing a column with two separate selective adsorbents utilized in the column of FIG. 1.

The chromatographic or adsorption column of this invention may be desirably provided in kit form generally indicated by the reference numeral 10 in FIG. 3 and comprising a test tube 11 and an adsorption column 12 fitting within the test tube. The kit may desirably include a second adsorption and detection column 14 which fits within the first adsorption column 12 as shown in FIG. 2. The test tube and columns may be made of plastic for throw-away convenience and to avoid contamination when handling toxic solutions. When identification or detection of the analyte is desired by fluorescent light, as will be further described, the column 14 may be made of glass.

The columns 12 and 14 may desirably be provided with two-way or one-way valves which provide for plunger type pressure to force a solution through the bottom of the columns into and through the packing material contained therein.

Figure 1:
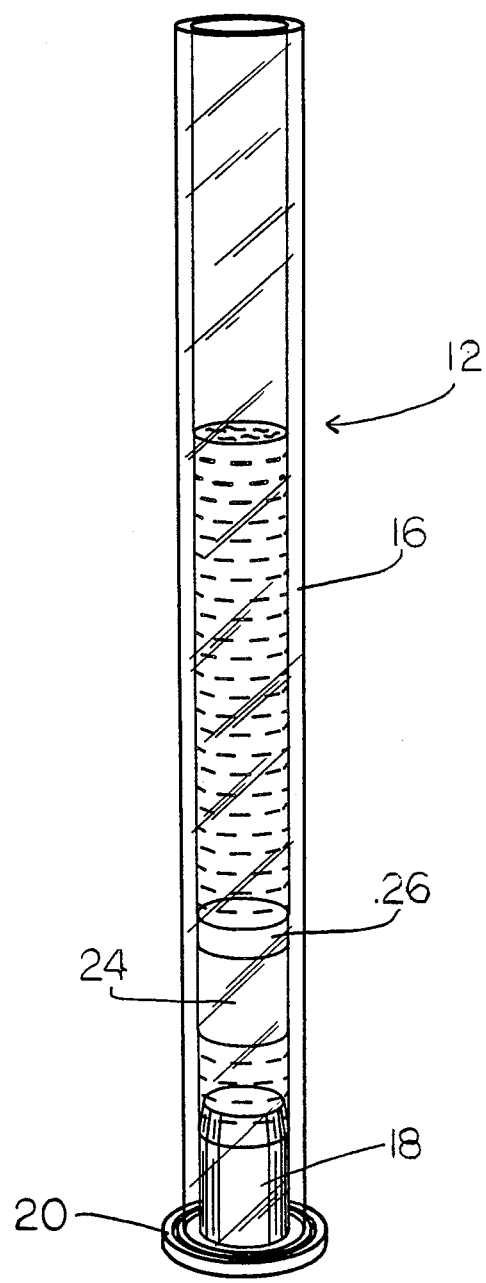
FIG. 1 is a perspective view showing the adsorption column with a single adsorbent.

The adsorption column 12 as best shown in FIGS. 1, 3 and 4 is of a two-way nature and is comprised of a tubular column element 16, a valve 18 fitting within the bottom of the column and a rubber like flange seal 20 which closely engages the inner wall of the test tube 11. Frit or inert packing material 22 as shown in FIG. 4 is employed to filter out solids. As shown in FIG. 1, an adsorbent packing material 24 may be inserted in the column topped by a frit layer 26 as desired. The column functions as it is inserted into the test tube to force a test solution 28 by plunger action through the valve at the bottom of the column through the frit 22 and the adsorbent packing 24 to provide a semi-purified solution 30 which may be further analyzed as will be described below for detection of analytes. The semi-purified solution may be decanted or poured out as desired or the column may be tilted to break the vacuum seal and withdrawn. If the seal is not broken the semi-purified solution will be drawn back into the test tube.

For convenience a column with a one-way valve 32 as shown in FIG. 5 may be employed. This valve employs a similar rubber-like flange seal 20, but has a valve housing 34 which contains frit 22 and a one-way or check valve member 36 which is adapted to open from a valve seat 38 when the column is inserted into the test tube and fluid is forced through the valve and close against the valve seat when the column is withdrawn. A flexible web 40 connects the valve member to the inner part of the valve housing to permit the valve member to open and close against the valve seat. By virtue of the one-way valve construction the column may be withdrawn from the test tube with the semi-purified solution therein.

For further analysis, and as will be more fully described below, the second adsorption column 14 shown in FIG. 2 may be employed. This column may be of the same construction as column 12 as described above and fits closely within column 12. It is designed to contain one or a plurality of selective adsorbent layers 42 and 44 bounded by frit layers 46 and 48. It is employed to force the semi-purified solution in column 12 through the column 14 for selective adsorption and detection of analytes as will more fully appear.

METHOD OF USE

In use the plunger action of the adsorption column acting as a plunger or piston provides the required pressure to force the test solution through the adsorption column 12 or 14. The rubber-like flange or seal does not allow any air or solution to move up the walls of the test tube but forces the solution through frit 22 in the center of the one-way or two-way valve employed in the adsorption column. When the desired amount of semi-purified solution has passed through the packing material into the column 12, the column may be slowly withdrawn where the one-way valve is employed or decanted or otherwise emptied in the case of the two-way valve. The column 12 may be slowly withdrawn in order that little pressure need be exerted to withdraw it. The frit 22 in the valve housing in this case also acts as a one-way valve which allows solution to flow into the column when greater pressure is exerted as the column is inserted into the tube but not out as the column is gently withdrawn to permit the semi-purified solution to remain in the column.

A rapid preparation of a desired volume of the semi-purified solution is readily obtained without the use of sophisticated force-applying equipment that might be obtainable only in a laboratory and difficulty accessible in the field. Both solid and soluble interferences such as pigments, xanthophyll, fluorescent compounds, fats and low polar materials and most carbohydrates and proteins are readily removed from the semi-purified solution. Gravity flow for field or other on site analysis is not desirable because of the time involved and is not adequate to force a test solution through small particle size adsorbent packing at a desirable speed. A further advantage of the test tube and adsorption kit of this invention is that the components through their inexpensive cost are disposable. Thus when the analytes are toxic mycotoxins or the like, a minimum of contact with the solution by the analyst is required.

The adsorption kit of this invention can be expeditiously employed for adsorption and detection of various analytes. It is especially useful, as an example, in a method for testing for five commonly found mycotoxins or mold toxins which are known to contaminate human foods and animal feeds. Such mycotoxcins as aflatoxin B-1, B-2, G-1 and G-2 and zearalenone are dangerous toxins and their early detection is important to the public and industry. The aflatoxins are some of the most potent carcinogens known and zearalenone is a hormonal toxin which causes huge financial losses to the pork industry.

The sample extract purification step of this method requires about ten seconds compared to the 1-2 hours required for sample extract purification when official methods of the Association of Official Analytical Chemists (A.O.A.C.) are used for these same toxins. Also, the A.O.A.C. methods require the use of about 200 ml of hazardous solvents per sample compared to the 5-15 mls of solution required by the method of this invention.

The total method consists of:
1. Place 25 grams of the feed sample and 100 ml of acetonitrile/water (9/1) in a blender jar.
2. Blend for 3 minutes.
3. Transfer about 5 ml of sample extract to the test tube 11 which has a 10 mm i.d.
4. Slowly force the adsorbent column 12 into the test tube 11 until the top of the column is about half full of semi-purified extraction solution.
5. Transfer 2.0 ml of semi-purified extract to a 40 ml centrifuge tube. Evaporate the solvents under vacuum or nitrogen using a 60 degree C water bath.
6. Dissolve the residue in 0.5 ml of benzene/acetonitrile (97/3).
7. Quantitate the aflatoxins are zearalenone by known methods using thin layer chromatography (TLC).

MODIFIELD DETECTION

The kit can be used in a second way. In some instances, particularly for field use, it is desirable to band the analyte to be detected on a packing material and detect it while it is there. In this case, very selective packing materials should be used, which attach the analyte or analytes adsorbent or a plurality of adsorbents and does not attract other chemicals or analytes.

The kit of this invention can be used in a modified method for the later stages of detection above described. The method is particularly useful in the field for early detection of analytes on a selective adsorbent. In this method, a highly selective adsorbent is employed to adsorb the analyte and not adsorb other analytes. Where a plurality of analytes are desired to be adsorbed, it will be understood that a series of selective adsorbents may be utilized.

In this method the column 12 with the semi-purified extract is employed from step 4 above and the extract is subjected to a further adsorption by inserting the second column 14 as shown in FIG. 2 into column 12. This insertion forces the semi-purified extract into the column 12. The adsorbent 42 is designed as a selective adsorbent for aflatoxin while the adsorbent 44 is a selective adsorbent for zearalenone.

The pumping or forceful action effected by the insertion of column 14 into column 12 and the seal provided by the rubber-like flange 20 cause the extract to flow into column 14 past the two adsorbent layers 42 and 44 to fill the detection column 14. Column 14 is then removed and placed under a long wave ultraviolet light, such as from a mercury light, which causes both the aflatoxin and zearalenone to fluoresce, blue and yellow, respectively. A positive indication of the foregoing fluorescence indicates the presence of one or the other or both of these mycotoxins. In this detection, the ultraviolet light may desirably employ a wavelength of about 365 nanometers for aflatoxin and zearalenone. Zearalenone may also desirably be detected at a wavelength of about 224 nanometers. A polycarbonate test tube should be used since light of a wavelength of 224 nanometers will not pass through glass.

The above uses of the kit for a purification column and a detection column provides a rapid, safe and inexpensive field test for analytes and especially mycotoxins. The kit comprising the purification column and detection column may be simply employed by non-scientific personnel such as feed and grain mill personnel, farmers and ranchers with a minimum exposure to the toxins.

There is set forth below two examples illustrating two analytical methods which demonstrate the use of the kit of this invention. The first example is that of use as a purification or cleanup adsorption column in which analytical interferences are attached or adsorbed by the packing material while the analytes to be detected remain in the semi-purified solution or extract. The second example illustrates the use as a detection column in which the analytes to be detected are detected and measured while bonded to the packing material.

EXAMPLE I

Use of a packed filter tube as a cleanup column in a thin layer chromatographic method for detection of aflatoxins and zearalenone in corn. The column 12 is "packed" with 1.0 gram of silica gel which has octadecyl silane bonded to it, commonly known as C-18 packing. The method consists of:
1. Place 25 grams of sample in blender, add 100 mls of 9/1 $CH_3CN/H_2O$.
2. Blend for 3 minutes and filter.
3. Mix 5 ml filtrate with 4 ml distilled $H_2O$.
4. Transfer the 9 ml sample solution to test tube 11.
5. Slowly push the C-18 cleanup adsorption column 12 to the bottom of the test tube forcing the sample solution through the C-18 packing 24 in column 12.
6. Remove the cleanup column from the test tube and transfer the purified sample solution to a 40 ml test tube.
7. Add 3 ml of fresh $CH_3CN/H_2O$ (50/50) to the test tube and push this solution through the C-18 packing in the cleanup column; combine the solution above the C-18 packing with the 9 ml in the 40 ml test tube.
8. Extract the toxins from the $CH_3CN/H_2O$ with two 5 ml portions of $CHCl_3$ by thoroughly mixing on a test tube shaker - combine the two portions of $CHCl_3$ in a 40 ml centrifuge tube.
9. Evaporate chloroform to dryness. Dissolve the residue in benzene/$CH_3CN$ (97/3) and spot appropriate amounts of sample solution and standard solutions on a 10×20 cm silica gel TLC plate.
10. Develop the plate in 9/1 $CHCl_3$/Acetone.
11. Examine the TLC plates under long wave ultraviolet light. Zearalenone appears as a yellow fluorescent spot at about 0.8 Rf. Aflatoxins B-1, B-2, G-1, and G-2 appear as bluish fluorescent spots from 0.4 (G-2) to 0.5 (B-1) Rf.

EXAMPLE II

Use of packed detection column 14 in a screening method for aflatoxins in corn.

Both the Romer Minicolumn Method and the Holiday-Velasco Minicolumn Method for aflatoxin are official methods of the A.O.A.C. The Romer method is set forth in Official Methods of Analysis (1984) 14th edition; A.O.A.C., Arlington, VA §§26.014-26.019 while the Holiday-Velasco method is set forth in §§26.020-26.025. Both of these methods use a small chromatographic detection column or minicolumn in their final step. A few mls of chloroform (Romer Method), or benzene (Holiday-Velasco Method), followed by the 3 mls of elution solvent are allowed to gravity drain through the minicolumn. A longwave ultraviolet lamp is then shined on the minicolumn. If a blue fluorescent band is seen at the top of the Florisil (activated magnesium silicate) layer, the test is positive for aflatoxin; if no blue band is evident, the test is negative.

The minicolumn used in the official methods has two drawbacks. The first drawback is that gravity draining of a solution through the minicolumn requires 10-20 minutes. The second drawback is that the use of pressure to speed up the flow requires vacuum or pressurizing equipment including valves and gauges.

The packed column 14 is used as a detection column by inserting the minicolumn adsorbents in reverse order. Thus, the filter tube detection column contains from bottom to top: 5-7 mm $CaSO_4$, 8-10 mm neutral alumina, 18-20 mm silica gel, 5-7 mm Florisil, and 5-7 mm of $CaSO_4$. The $CaSO_4$ picks up moisture and prevents the other layers from becoming moist, neutral alumina adsorbs some pigments and silica gel retains other analytical interferences. The aflatoxin bands on the first particles of Florisil it comes in contact with (in this case, the lower end of the Florisil layer). The column is made of glass, instead of plastic, since plastic will not allow ultraviolet light to penetrate it.

In this example chloroform or benzene is placed into a test tube, and the detection column is pushed to the bottom of the test tube. The detection column is removed and emptied of solvent; the proper volume of elution solvent is added to the test tube or employed in column 12 and the detection column 14 is again forced to the bottom of the test tube or column. The detection column is removed, emptied of solvent and viewed under long wave ultraviolet light. If a blue fluorescent band is detected at the bottom of the Florisil layer, the test is positive for aflatoxin. If no blue band is evident, the test is negative.

The advantage of using the detection column and kit of this invention is both speed and simplicity, i.e. speed over the gravity flow column resulting in a 10-20 minute reduction of analysis time and simplicity over a vacuum or gas pressure system since the column, itself, contains its own pressure system.

Various changes and modifications may be made within this invention as will be apparent to those skilled in the art. Such changes and modifications are within the scope and teaching of this invention as defined in the claims appended hereto.

What is claimed is:

1. A method for purification of analytes in a solution which comprises placing said solution in a test tube, inserting a pressure exerting adsorption column having a resilient seal closely engaging an inner wall of said test tube to force said solution into said column through a bottom opening in said column past a filter member and past an adsorbent packing material to adsorb interference material to provide semi-purified solution in which solid and soluble interferences are removed, withdrawing said semi-purified solution and subjecting said solution to a selective detection procedure for further analysis of analytes therein.

2. The method of claim 1 in which the detection is determined for separate analytes to indicate their presence by application of fluorescent lights of different wave lengths for separate analytes.

3. The method of claim 1 in which the selective detection is determined to indicate the presence of said analytes by chromatography.

4. The method of claim 1 in which the selective detection is determined to indicate the presence of said analytes by adsorption.

5. The method of claim 1 in which said selective detection is determined by analyzing said semi-purified solution in a test tube or the like by inserting a second pressure exerting adsorption column into said last named test tube, said second column having a resilient seal closely engaging an inner wall of said last named test tube to force said semi-purified solution into said second column through a bottom opening in said column past a selective adsorbent packing material having a selective adsorbent capacity for the analyte to be detected and testing said selective adsorbent for the presence of said analyte.

6. A method for purification of analytes in a solution which comprises placing said solution in a test tube, inserting a first pressure exerting adsorption column having a resilient seal closely engaging an inner wall of said test tube to force said solution into said first column through a bottom opening in said first column past a filter member and past an adsorbent packing material to adsorb interference material to provide a semi-purified solution and withdrawing said semi-purified solution for further analysis of analytes therein, said analytes in the semi-purified solution being detected by inserting a second pressure exerting adsorption column into said first column, said second column having a resilient seal closely engaging an inner wall of said first column to force said semi-purified solution into said second column through a bottom opening in said column past a selective adsorbent packing material having a selective adsorbent capacity for the analyte to be detected and testing said selective adsorbent for the presence of said analyte.

7. The method of claim 6 in which the selective adsorbent is one that selectively adsorbs a mycotoxin and detection is determined by shining a light thereon to indicate presence of said mycotoxin by fluorescence.

8. The method of claim 7 in which said mycotoxin is aflatoxin and the light has a wavelength of about 365 nanometers.

9. The method of claim 7 in which said mycotoxin is zearalenone and the light has a wavelength of at least one of about 365 and 224 nanometers.

10. The method of claim 6 in which a plurality of separate selective adsorbents are employed in said second column for separate adsorption of different analytes.

11. The method of claim 10 in which the selective adsorbents selectively adsorb aflatoxin and zearalenone and detection is determined by shining a light thereon to indicate presence of aflatoxin and zearalenone by fluorescence.

12. The method of claim 11 in which a light having a wavelength of about 365 nanometers is employed for aflatoxin and a light having a wavelength of about 224 nanometers is employed for zearalenone.

13. The method of claim 10 in which the separate selective adsorbents are fluorescently active and responsive to adsorption by the separate analytes to be detected and the adsorbents are subjected to fluorescent lights of different wave lengths to determine the adsorption of said analytes.

14. The method of claim 6 in which the selective adsorbent is fluorescently active and responsive to adsorption by the analyte to be detected, and the adsorbent is subjected to fluorescent light to determine the adsorption of said analyte.

15. A method for purification of mycotoxin analytes in a solution containing at least one of feed grains and foodstuffs which comprises placing said solution in a test tube, inserting a pressure exerting adsorption column having a resilient seal closely engaging an inner wall of said test tube to force said solution into said column through a bottom opening in said column past a filter member and past an adsorbent packing material to adsorb interference material to provide a semi-purified solution in which solid and soluble interferences are removed, withdrawing said semi-purified solution and subjecting said solution to a selective detection procedure for further analysis of mycotoxin analytes therein.

16. The method of claim 15 in which the selective detection is determined to indicate presence of said mycotoxin by fluorescence.

17. The method of claim 16 in which said mycotoxin is aflatoxin and the light has a wavelength of about 365 nanometers.

18. The method of claim 16 in which said mycotoxin is zearalenone and the light has a wavelength of at least one of about 365 and 224 nanometers.

19. The method of claim 16 in which the detection is determined to indicate presence of aflotoxin and zearalenone by fluorescence.

20. The method of claim 19 in which a light having a wavelength of about 365 nanometers is employed for aflotoxin and a light having a wavelength of about 224 nanometers is employed for zearalenone.

21. The method of claim 15 in which the selective detection is determined to indicate the presence of said mycotoxin analytes by chromatography.

22. The method of claim 15 in which the selective detection is determined to indicate the presence of said mycotoxin analytes by adsorption.

* * * * *